United States Patent [19]

Zallie et al.

[11] Patent Number: 5,281,432
[45] Date of Patent: Jan. 25, 1994

[54] METHOD OF MAKING FOODS CONTAINING SOLUBLE HIGH AMYLOSE STARCH

[75] Inventors: James Zallie, Hillsborough; James Eden, East Millstone; James Kasica, Whitehouse Station; Chung-Wai Chiu, Westfield; Gary Zwiercan, Califon; Gary Plutchok, Somerset, all of N.J.

[73] Assignee: National Starch and Chemical Investment Holding Corporation, Wilmington, Del.

[21] Appl. No.: 893,582

[22] Filed: Jun. 2, 1992

Related U.S. Application Data

[63] Continuation of Ser. No. 597,918, Oct. 12, 1990, abandoned.

[51] Int. Cl.[5] .......................................... A23L 1/0522
[52] U.S. Cl. ....................................... 426/549; 426/7; 426/443; 426/578; 426/579; 426/661; 127/71
[58] Field of Search ................... 426/7, 443, 549, 578, 426/579, 661; 127/71

[56] References Cited

U.S. PATENT DOCUMENTS

| | | | |
|---|---|---|---|
| Re. 27,531 | 12/1972 | Murray et al. | 99/100 |
| 3,086,890 | 4/1963 | Sarko et al. | 127/69 |
| 3,515,591 | 6/1970 | Feldman et al. | 127/32 |
| 3,527,646 | 8/1970 | Schieck et al. | 99/166 |

(List continued on next page.)

FOREIGN PATENT DOCUMENTS

| | | | |
|---|---|---|---|
| 0138010 | 5/1989 | European Pat. Off. | C08B 30/14 |
| 0366248 | 5/1990 | European Pat. Off. | A23B 7/10 |
| 0366898 | 5/1990 | European Pat. Off. | C08B 30/14 |
| 0372184 | 6/1990 | European Pat. Off. | |
| 8910702 | 11/1989 | PCT Int'l Appl. | A23L 1/217 |

OTHER PUBLICATIONS

"Effect of Starch on Pasta Dough Rheology and Spaghetti Cooking Quality," *Cereal Chemistry*, 56 (3):190–195 by J. E. Dexter and R. R. Matsuo (1979).
Anon, Ulta-Set LT high performance starch, National Starch and Chemical Corporation, Sep. 1989.
Zallie, The role and function of specialty starches in the confection industry, National Starch and Chemical Corporation, Mar. 1989.
Anon, HYLON VII, National Starch and Chemical Corporation, Technical Service Bulletin, 1988.
Anon, HI-SET 60, National Starch and Chemical Corporation, Technical Service Bulletin, 1988.
Anon, CRISP FILM, National Starch and Chemical Corporation, Technical Service bulletin, 1988.
Anon, HI-SET 30, National Starch and Chemical Corporation, Technical Service Bulletin, 1987.
Anon, HI-SET C, National Starch and Chemical Corporation, Technical Service Bulletin, 1988.
Anon, HI-SET Starches, National Starch and Chemical Corporation, Technical Service Bulletin, 1985.
Anon, HI-SET CHG, National Starch and Chemical Corporation, Technical Service Bulletin, 1987.
Anon, HYLON V, National Starch and Chemical Corporation, Technical Service Bulletin, 1988.
Anon, HI-SET 377, National Starch and Chemical Corporation, Technical Service Bulletin, 1987.

*Primary Examiner*—Helen F. Pratt
*Attorney, Agent, or Firm*—Mary E. Porter

[57] ABSTRACT

The present invention provides foods containing soluble high amylose starch selected from: (i) spray-dried, non-granular starch, characterized in that the starch is substantially non-crystalline, substantially nonretrograded, and fully predispersed; (ii) spray-dried, uniformly gelatinized starch in the form of granular indented spheres, with at least a majority of the granules being whole and unbroken, the starch granules being in the form of loosely-bound agglomerates or individual granules; (iii) enzymatically debranched gelatinized starch, comprising at least 40% amylose; and (iv) mixtures thereof.

The foods prepared with soluble high amylose starch are characterized by one or more of the following beneficial properties: stronger gels, improved appearance, improved adhesion, air-, oil- and/or water-impermeable surfaces; and improved textures. These foods are easier to prepare when they contain the soluble high amylose starches herein, since these starches, in contrast to high amylose starches used in the same foods under normal preparation temperatures, can be completely and thoroughly dispersed in the food formulation using hot or cold water, without chemical modification of the starch.

5 Claims, No Drawings

U.S. PATENT DOCUMENTS

| | | | |
|---|---|---|---|
| 3,630,775 | 12/1971 | Winkder | 127/71 |
| 3,650,770 | 3/1972 | Marotta et al. | 127/34 |
| 3,666,557 | 5/1972 | Jensen et al. | 127/32 |
| 3,751,268 | 8/1973 | Van Patten et al. | 99/100 |
| 3,777,039 | 12/1973 | Patten et al. | 426/62 |
| 3,792,176 | 2/1974 | Patten et al. | 426/157 |
| 3,956,519 | 5/1974 | Evans et al. | 426/564 |
| 3,974,742 | 2/1974 | Harris et al. | 426/302 |
| 3,987,210 | 10/1976 | Cremer | 426/550 |
| 4,076,846 | 2/1978 | Nakatsuka et al. | 426/62 |
| 4,238,517 | 12/1980 | Bosley et al. | 426/250 |
| 4,251,556 | 2/1981 | Burkwall et al. | 426/332 |
| 4,272,553 | 6/1981 | Bengtsson et al. | 426/241 |
| 4,280,851 | 7/1981 | Pitchon et al. | 127/33 |
| 4,487,786 | 12/1984 | Junge | 426/302 |
| 4,529,607 | 7/1985 | Lenchin et al. | 426/94 |
| 4,544,563 | 10/1985 | Lechthaler | 426/276 |
| 4,562,082 | 12/1985 | Morimoto | 426/104 |
| 4,595,597 | 6/1986 | Lenchin et al. | 426/555 |
| 4,600,472 | 7/1986 | Pitchon et al. | 159/4.4 |
| 4,640,837 | 2/1987 | Coleman et al. | 426/94 |
| 4,675,197 | 6/1987 | Banner et al. | 426/292 |
| 4,755,392 | 7/1988 | Banner et al. | 426/555 |
| 4,767,630 | 8/1988 | Silver et al. | 426/102 |
| 4,806,378 | 2/1989 | Ueno et al. | 426/643 |
| 4,810,660 | 3/1989 | Willard | 426/272 |
| 4,869,920 | 9/1989 | Kawana et al. | 426/643 |
| 4,871,398 | 10/1989 | Katcher et al. | 127/71 |
| 4,874,628 | 10/1989 | Eden et al. | 426/578 |
| 4,877,629 | 10/1989 | Stypula et al. | 426/302 |
| 4,910,039 | 3/1990 | Fujita et al. | 426/652 |
| 4,937,091 | 6/1990 | Zallie et al. | 426/582 |
| 4,944,955 | 7/1990 | Bassa et al. | 426/579 |
| 4,948,615 | 8/1990 | Zallie et al. | 426/578 |
| 4,959,230 | 9/1990 | Wyss et al. | 426/102 |
| 4,971,723 | 11/1990 | Chiu | 426/661 |

METHOD OF MAKING FOODS CONTAINING SOLUBLE HIGH AMYLOSE STARCH

This application is a continuation of application Ser. No. 07/597,918, filed Oct. 12, 1990, abandoned.

BACKGROUND OF THE INVENTION

This invention relates to foods which have been formulated to contain soluble high amylose starch. The starch is selected from: a spray-dried, non-granular, high amylose starch, characterized in that the starch is substantially non-crystalline, substantially non-retrograded, and fully predispersed; a spray-dried, uniformly gelatinized, high amylose starch in the form of granular indented spheres, with at least a majority of the granules being whole and unbroken, these starch granules being in the form of loosely-bound agglomerates or individual granules; and an enzymatically debranched, gelatinized starch, comprising at least 40% amylose. These starches are soluble in hot or cold water and cooking is not required to formulate foods containing these starches.

As used herein, "soluble" means that the high amylose starches in powdered form may be readily hydrated and dispersed in hot or cold water or other aqueous medium to provide a starch solution in the form of a complex colloidal dispersion, rather than a true molecular solution.

Native high amylose starches are corn starches from hybrid varieties of corn which contain at least about 40% amylose. In contrast, ordinary corn starch typically contains about 28% amylose. As used herein, "high amylose starch" includes the starch from hybrid strains of corn, as well as other starches which contain added isolated amylose, or which have been enzymatically debranched to yield a starch comprising at least about 40% amylose. This debranched starch may comprise both native long chain amylose and short chain amylose generated by debranching amylopectin molecules.

Because amylose, a linear polymer, readily aligns or associates through hydrogen bonding, starches containing large amounts of amylose will form more rigid gels and stronger, tougher films, and will provide surfaces having reduced air, water and oil absorption and migration in food applications, relative to ordinary starches which typically contain much less than 40% amylose. Other advantages include improved binding properties where the starch primarily functions as an adhesive and the related property of improved cling or adhesion between dissimilar food substrates. The unique binding, structural and textural characteristics of the high amylose starches make them useful as protein replacers, especially caseinate replacers, in foods.

A process for improving deep fried potato products, including potato chips, french fried potatoes, and specialty potatoes, wherein the potatoes are coated with an aqueous dispersion of a high amylose starch prior to frying, is disclosed in U.S. Pat. No. Re. 27,531, reissued Dec. 12, 1972, to Murray, et al. The potato products are characterized by a high degree of crispness which is retained for long periods, superior strength and rigidity, resistance to breakage without undesirable toughness, reduced absorption of oil during frying, reduced variation in the amount of oil absorption, little color variation, and excellent flavor and storage characteristics.

An improved batter mix for preparing coated prefried, microwavable-foods, wherein the batter contains, on a batter mix solids basic, about 50-80% of a high amylose flour containing at least 50% amylose, is disclosed in U.S. Pat. No. 4,595,597, issued Jun. 17, 1986, to Lenchin, et al. The batter containing the high amylose flour provides a crisp and appealing outer coating in foods formulated for use in the microwave oven. The high amylose flour batter also provides good adhesion and cohesion to the food and acceptable color.

A batter for Use on frozen, prefried, convenience foods, wherein the batter comprises, on a batter dry mix basis, about 50 to 80% of a high amylose flour containing at least 50% amylose, is disclosed in U.S. Pat. No. 4,529,607, issued Jul. 16, 1985, to Lenchin, et al. The batter provides improved crispness in the food coating after conventional cooking.

Improved pet foods, of the semi-moist variety, wherein starches, including modified high amylose corn starch, are employed as dough modifiers, is disclosed in U.S. Pat. No. 4,251,556, issued Feb. 17, 1981, to Burkwall, Jr., et al. The starch advantageously replaces, in part, caseinates as a binder in the pet food.

A formulated french fried potato product produced from dehydrated potato granules or flakes with a binder, comprising a high amylose starch and a cold water dispersible starch or gum, is disclosed in U.S. Pat. No. 3,987,210, issued Oct. 19, 1976, to Cremer. The high amylose starch component, preferably containing at least about 35% amylose, functions by retrograding to form a film or oil barrier on the french fried dough so that the dough does not absorb large quanties of frying oil. The high amylose starch also adds strength to the french fried product during and after frying. Useful high amylose starches include granular or ungelatinized high amylose starch containing at least 55% amylose, and, optionally, ester and ether derivatives of the starches; and amylose obtained by fractionating starch and derivatives thereof.

Certain high amylose starches and starch blends have been successfully employed as caseinate replacers in imitation cheeses. The starches useful as caseinate replacers differ from starches and flours which have been used in various cheese products as thickeners, binders, and the like. Unlike the thickeners and binders, the caseinate replacement starches provide the texture, thermoreversibility (melt) and emulsification characteristics of caseinates in imitation cheeses. A starch characterized by thermoreversibility forms a gel when a cooked aqueous starch dispersion is cooled, which gel melts upon reheating and sets again upon cooling.

U.S. Pat. No. 4,608,265, issued Aug. 26, 1986, to Zwiercan, et al., discloses an imitation cheese, wherein 25 to 50% of the caseinate as replaced by pregelatinized modified high amylose starches, preferably converted and derivatized. The starch has an amylose content of at least 40% and is preferably selected from the group consisting of derivatized starch, converted starch, converted and derivatized starch and crosslinked starch. The high amylose starch may be mixed with up to 80%, by weight, of a low amylose starch (leas than 40% amylose). U.S. Pat. No. 4,695,475, issued Sep. 22, 1987, to Zwiercan, et al., discloses an imitation cheese wherein up to 100% of the caseinate is replaced by a pregelatinized, converted and derivatized high amylose starch.

The formulation of foods with the high amylose starches known in the art disadvantageously requires much higher cooking temperatures than the temperatures required for cooking other starches. Due to the highly bonded linear structure of high amylose starches, full and effective gelatinization of high amylose starches typically requires cooking temperatures of about 154°–171° C., when the starch contains about 70% amylose. Thus, to obtain high amylose starches, or foods containing such starches, which are soluble in hot or cold water, super atmospheric cooking temperatures are usually required. Furthermore, traditional methods of starch pregelatinization typically produce high amylose starches that are retrograded, or have crystalline portions or are otherwise incapable of full dispersion, or are degraded such that their functional benefits are substantially reduced.

For example, a method for preparing drum-dried, non-granular, pregelatinized isolated potato amylose is described in U.S. Pat. No. 3,086,890, issued Apr. 23, 1963, to A. Sarko, et al. The starch slurry is heated to a temperature from just above boiling to 191° C. (375° F.) and a pressure of about 5 to 140 psi for 1 to 60 minutes. It is then drum-dried at 110°–200° C. (230°–392° F.) for 40–75 seconds and the resulting sheet is pulverized to a dry, porous, white fluffy powder. Sarko's assignee subsequently disclosed in U.S. Pat. No. 3,515,591, issued Jun. 2, 1970, to Feldman, et al., that the product of Sarko's drum-drying method slowly retrogrades upon storage and is unsuited for use in packaged foods. The Feldman patent teaches a different method for preparing cold water soluble high amylose starch which disadvantageously requires the high amylose starch to be solubilized at 140°–170° C. and mixed with an aqueous suspension of gelatinized starch before drying.

In the alternative, high amylose starches have been modified by derivatization and conversion to enhance their gelatinization and dispersibility characteristics. The use of these "modified starches" is undesirable in food products that are advertised as "natural" products. Gel strength and water resistance qualities of the modified high amylose starches also are reduced in proportion to the amount of modification.

Accordingly, there is need for foods containing soluble high amylose starch which can be formulated without cooking or without using a chemically modified starch, and can be prepared by dispersing the soluble high amylose starch in hot or cold water, before, during, or after food formulation.

SUMMARY OF THE INVENTION

The present invention provides an improved method for preparing foods comprising the step of adding to the foods a soluble high amylose starch selected from the group consisting of: (i) spray-dried, non-granular starch, characterized in that the starch is substantially non-crystalline, substantially non-retrograded, and fully predispersed; (ii) spray-dried, uniformly gelatinized starch in the form of granular indented spheres, with at least a majority of the granules being whole and unbroken, the starch granules being in the form of closely-bound agglomerates or individual granules; and (iii) enzymatically debranched, gelatinized starch, comprising at least 40% amylose; and (iv) mixtures thereof.

Foods prepared with soluble high amylose starch are characterized by one or more of the following beneficial properties: stronger gels, improved appearance, improved adhesion, air-, oil- and/or water-impermeable surfaces; and improved textures. These foods are easier to prepare when they contain the soluble high amylose starches herein, which in contrast to high amylose starches used in the same foods at normal cooking temperatures, are completely and thoroughly dispersed in the food formulation using hot or cold water.

DESCRIPTION OF THE PREFERRED EMBODIMENTS

The use of particular methods for providing pregelatinized granular or non-granular soluble high amylose starches is a significant feature of the invention. The high amylose starches are cooked and spray-dried under conditions which provide pregelatinized starches with unique properties. Stabilized, unconverted and/or converted high amylose starches (i.e., derivatized starches such as ethers or esters and/or the crosslinked products) may be used as the main component provided the organoleptic or functional qualities of the foods are not adversely affected. The starch may be derived from any high amylose plant source which contains concentrations of about 40–100% amylose, including, for example, high amylose corn and wrinkled pea. The preferred starches are those derived from high amylose corn hybrids.

High amylose starches which are obtained from special hybrids of corn, barley and pea may contain as much as 70% amylose and are more expensive and more difficult to isolate than the typical native starches from more readily available sources such as corn, potato, wheat, rich, tapioca and the like. Most of the readily available starches contain less than 30% amylose. However, a starch containing a high percentage of short chain amylose may be produced from any of the more readily available amylopectin-containing starches by treating the starch with an enzyme capable of cleaving the alpha-1,6-D-glucosidic linkages of the amylopectin. This enzymatic treatment cleaves the branch points on the amylopectin molecule, yielding a mixture of short chain amylose and partially debranched amylopectin, together with any remaining amylopectin or any long chain amylose present in the untreated starch. For use herein, the total amylose content of the debranched starch must be at least 40%, by weight.

Simultaneous Cooking/Spray-Drying Process

A method for preparing suitable spray-dried, granular pregelatinized starches is described in U.S. Pat. No. 4,280,851, issued Jul. 28, 1981, to E. Pitchon, et al., which is hereby incorporated by reference. In this process a slurry of the granular starch is cooked or gelatinized in an atomized state. A slurry of the starch which is to be cooked is injected through an atomization aperture in a nozzle assembly to form a relatively finely-divided spray. A heating medium is also injected through an aperture in the nozzle assembly into the spray of atomized material so as to heat the starch to a temperature effective to gelatinize the starch. An enclosed chamber surrounds the atomization and heating medium injection apertures and defines a vent aperture positioned to enable the heated spray of starch to be atomized again as the starch exits the chamber. Thus, it is a dual-atomization process. The arrangement is such that the lapsed time between passage of the spray of starch through the chamber, i.e., from the atomization aperture and through the vent aperture defines the gelatinization time of the starch. The resulting spray-dried pregelatinized starch comprises uniformly gelatinized starch granules in the form of indented spheres, with a majority of the granules being whole and unbroken and swelling upon rehydration. Nozzles suitable for use in the preparation of these starches are also described in U.S. Pat. No. 4,610,760, issued Sep. 9, 1986, to P. A. Kirkpatrick, et al. A process for agglomerating these starches is described in U.S. Pat. No. 4,871,398, issued Oct. 3, 1989, to Ketcher, et al.

A single-atomization method for preparing suitable spray-dried, substantially pregelatinized starch is described in U.S. patent application Serial No. 07/471,141, filed Jan. 26, 1990, by R. Rubens, which is hereby incorporated by reference.

Drum-drying processes, such as the one disclosed in the Sarko patent, have not been successfully used to solubilize the native or isolated long chain amyloses due to retrogradation problems. However, drum-drying may be used to solubilize high amylose starches wherein the starches comprise about 40% short chain amylose (i.e., the debranched starches herein). Thus, drum-drying may be used to dry only the enzymatically debranched soluble high amylose starches herein, or blends thereof.

Enzymatic Debranching Process

Starches suitable for enzymatic treatment herein include any amylopectin-containing starch that is susceptible to attack by a debranching enzyme, such as pullulanase, with the resultant hydrolysis of the alpha-1,6-D-glucosidic bond. Suitable starches include corn, potato, sweet potato, wheat, rice, sago, tapioca, sorghum, waxy maize, smooth pea, Canadian pea, and the like.

The starch is pregelatinized before enzyme treatment to provide a uniformly debranched starch. It may be used in a dried form or as an aqueous dispersion following debranching to form foods having desirable textural properties. Numerous methods of pregelatinizing starch, such as jet-cooking, drum-drying and steam injection atomization processes, are known in the art and may be used before debranching the starch. In a preferred embodiment, the starch is slurried in water and jet-cooked at approximately 300° F. (149° C.) to instantaneously gelatinize the starch.

The debranched starch, particularly the fully debranched starch, remains soluble and does not crystallize or retrograde if the starch solution or dispersion as dried immediately following the completion of the enzyme treatment. Thus it is preferred to dry the debranched starch as soon as practicable after debranching and preferably no more than 24 hours after debranching. If the debranched starch is obtained in a crystalline form, it may be solubilized by subjecting it to the coupled jet-cooking/spray-drying processes or the steam injection and atomization/spray-drying processes disclosed herein.

Converted debranched starches may be used herein. Conversion degrades the starch and reduces the starch's molecular weight and the viscosity of the cooked starch dispersions. Suitable conversion of the starches to thin-boiling or fluidity starches useful herein may be achieved by standard oxidative, heat, acid or alpha-amylase enzyme conversion techniques which are well known in the art. A method for starch conversion employing alpha-amylase enzyme is disclosed in U.S. Pat. No. 4,726,957, issued Feb. 23, 1988, to Lacourse, et al.

Following gelatinization, the starch is enzymatically treated by the methods disclosed in U.S. Pat. No. 4,937,091, issued Jun. 26, 1990, to Zallie, et al., which is hereby incorporated by reference. Enzymatic treatment must continue until the starch product comprises at least 40%, by weight, total amylose (short chain amylose and native or long chain amylose).

Coupled Jet-Cooking/Spray-Drying Process

Spray-dried, pregelatinized, non-granular, substantially non-crystalline, substantially non-retrograded high amylose starches can be provided by a novel continuous coupled jet-cooking/spray-drying process. This process is disclosed in U.S. patent application Ser. No. 07/242,657, filed Sep. 12, 1988, by Kasica, et al., now U.S. Pat. No. 5,131,953, which is hereby incorporated by reference. The process comprises the steps of:
  (a) forming a slurry or a paste comprising a converted or unconverted high amylose starch and water;
  (b) jet-cooking the aqueous slurry or paste of the starch with steam at a temperature sufficient to fully disperse or solubilize the starch;
  (c) immediately conveying and introducing the jet-cooked dispersion or solution into a nozzle of a spray-dryer at substantially the same temperature and pressure as the jet-cooking step;
  (d) atomizing the jet-cooked dispersion or solution through the nozzle of the spray-dryer;
  (e) drying the atomized Mist of the jet-cooked starch within the spray-dryer; and
  (f) recovering the jet-cooked and spray-dried starch as a water-dispersible or water-soluble powder.

The cooking temperature will depend upon whether a converted or unconverted starch is used. Typical temperatures are about 138°–177° C. (280°–350° F.).

The cooking chamber pressure used in the continuous coupled process typically ranges from 20 to 150 psig, and is the saturation pressure of steam at the temperature used plus the small incremental pressure needed to move the dispersion through the chamber. Cooking chamber pressures suitable for high amylose starches are 80 to 150 psig, most preferably 100 to 130 psig for a starch having an amylose content of about 70%.

An essential step in the above process is the conveying of the thoroughly cooked, substantially fully dispersed starch, under elevated pressure and temperature, to the spray-dryer atomization nozzle. In the preferred method, a low shear pneumatic nozzle is used, and the transfer is carried out at substantially the same temperature and pressure used in the jet-cooking. The transfer is carried out without any venting to the atmosphere. Atomization in a pneumatic nozzle may be used. The pressure of the atomization gas (steam or air) used must be sufficient for proper atomization into small droplets to allow rapid drying to an appropriate moisture without retrogradation.

Use of a pressure nozzle in the above process requires insertion of a high pressure pump (2,000 to 10,000 psig) between the jet-cooker and atomization nozzle. The temperature after passage through the high pressure pump should be maintained substantially equivalent to the jet-cooking chamber temperature. The pressure after the high pressure pump must be sufficient to properly atomize the cook to allow rapid drying to an appropriate moisture without retrogradation.

The spray-dried starch produced by the above process is non-granular and is characterized in that it is substantially non-crystalline and substantially non-retrograded. If the starch is to be converted or otherwise modified, these processes are typically carried out before the coupled jet-cooking/spray-drying process.

Acid conversion of high amylose starches is preferred due to the ease in handling and recovery during manufacturing afforded by a granular starch as opposed to starch in dispersed form as necessitated by enzyme conversion.

In the preparation of the converted starches by acid conversion, the granular starch is hydrolyzed to the desired degree in the presence of an acid, such as sulfuric or hydrochloric acid, at a temperature below the gelatinization temperature of the starch. The starch is slurried in water, and the acid (usually in concentrated form) is then added. Typically, the reaction takes place over an 8-16 hour period, after which the acid as neutralized with alkali (e.g., to pH of 5.5), and the starch is recovered by filtration.

It should be appreciated that the degree of conversion, as indicated by the water fluidity, is affected by the amount of acid or enzyme used as well as the time and temperature. The conversion conditions should be adjusted to provide an appropriate water fluidity.

Conversion procedures are conventional and well-known to those skilled in the art and described in such publications as *Handbook of Water-Soluble Gums and Resins*, Robert L. Davidson (Editor), Chapter 22: "Starch and Its Modifications" by M. W. Rutenberg, McGraw Hill Book Co. (New York) 1980.

Foods Containing Soluble High Amylose Starch

The soluble high amylose starches herein can be used in foods alone or in combination with starches other than high amylose starches (e.g., fluidity corn or tapioca starches). When a second starch component is present, the soluble high amylose starch must be present in an amount sufficient to provide foods with firm gels, crisp textures, impervious surfaces and other characteristic advantages of formulation with high amylose starch, without cooking, or at the cooking temperature normally used for the foods. Typically, the soluble high amylose starch is present in an amount of at least about 10 to 90%, preferably 25 to 60%, by weight, on a dry solids basis in the starch blend. In foods, the soluble high amylose starch or starch blend is present in an amount typically used for a particular food formulation. Depending on the food, the starch may be used at levels up to about 95%, on a dry weight basis.

When a combination of starches is used in the food formulations, the starches can be used as a one-part system, i.e., they may be solubilized by cooking both starches at the same time and then drying the resulting cooked starch blend by the methods disclosed herein. They also can be used as a two-part system in which case the soluble high amylose starch is prepared and added to the food formulation, and the second starch component is blended with the soluble high amylose starch or separately added to the food formulation. In a preferred embodiment, the soluble high amylose starches are dispersed in liquids slowly, with mixing or other shear so they are uniformly wetted and do not lump. They may be premixed or agglomerated to assist in uniform dispersion in liquids.

Starches preferred for use in combination with the soluble high amylose starches include corn, potato, sweet potato, rice, sago, tapioca, waxy maize, sorghum, or the like. Flours may also be used as a starch source.

The foods which can be advantageously prepared employing soluble high amylose starches include those foods previously formulated with high amylose starches (e.g., imitation cheeses) and foods which have not been formulated to contain high amylose starches (e.g., fresh fruits and vegetables which are cut and dipped in a soluble high amylose starch solution to prevent browning). For many in the latter group, high amylose starches were avoided because of the severe cooking conditions required for gelatinization of the high amylose starches known in the art. In the former group, food preparation is simplified and improved by use of the soluble high amylose starches, and food quality is enhanced by the selection herein of certain uniform, non-destructive methods of preparing soluble high amylose starches.

Among the foods which are improved herein are cominuted foods which require a binding or adhesive starch. Such cominuted foods include the gelled canned pet foods and prefabricated french-fried potatoes described herein. Also included herein are gelled foods, such as foods which are normally prepared with gelatin, and puddings, pie-fillings, and the like, cheese analogs and meat substitutes.

Also included is surimi, a gelled fish protein made from Alaskan pollock and other inexpensive fishes, which is a staple of the Japanese diet and a less expensive substitute for seafood such as crab, salmon and lobster. Methods for preparing surimi and related products (e.g., kamaboko) are disclosed in U.S. Pat. Nos. 4,806,378, issued Feb. 21, 1989, to Ueno, et al.; and U.S. Pat. No. 4,869,920, issued Sep. 26, 1989, to Kawana, et al. These gelled products are formulated from a variety of food ingredients and typical formulations include egg white protein to improve gel formation. The surimi disclosed herein is formulated to contain soluble high amylose starch as a gelling and binding agent in place of more expensive and complex systems employed in conventional surimi formulations. Furthermore, the surimi herein may be processed at typical surimi processing temperatures of 85°-95° C. which is well below the temperature needed to gelatinize high amylose starches (i.e., about 16° C.).

Another useful application in foods of the selected soluble high amylose starches herein is the replacement of at least a portion of the food proteins with these starches. Examples include the replacement of gelatin in gelled desserts prepared with hot water and the replacement of caseinates in pet foods as described herein.

The soluble high amylose starches herein are useful in the formulation of conventional and speciality pasta products. For example, these starches may be incorporated into noodles, such as fettucini, to provide resistance to softening upon prolonged cooking and standing and an al dente or firm noodle texture. These starches may be incorporated into Ramen (oriental) instant noodles. Manufacturers of Ramen noodles steam and fry the noodles before packaging, thereby providing convenience and a decrease in preparation time as compared with the regular noodles. Frying eliminates moisture in the noodles and secures a permanent form, however, it also creates a problem of picking up too much oil, typically 20 to 40 percent.

An improved Ramen noodle, prepared with soluble high amylose starch and having reduced oil pick-up and an improved, more elastic texture, is disclosed herein.

Other foods improved herein are coated foods. These include battered and breaded items such as chicken, vegetables, cheese, cominuted foods, and the like which may be prepared in conventional or microwave ovens, with or without the additional steps of par-frying and freezing. In addition to preparation by baking, these foods may be prepared by frying, with or without precooking and/or freezing.

Furthermore, the soluble high amylose starches may be incorporated into a bread dough prior to baking the bread which is then dried and used for bread crumb manufacturing. The resultant crumb is more effective than conventional bread crumbs in retarding the passage of moisture and water into or out of the food during processing and storage.

Surface coatings to retain moisture or oil or to impede migration of air, oil or water between the environment and the food are also included herein. Such coatings include the cookie predust, french-fried potato dip, and fresh fruit and vegetable anti-browning dip exemplified herein. The batters, breadings and surface coatings prepared with soluble high amylose starch advantageously provide an exterior food texture that is more crisp, brittle and impervious than conventionally prepared food surface coatings.

The group of foods described above exemplifies preferred uses of soluble high amylose starches in food applications. The practitioner may readily apply these teachings to other applications in the art. Thus, other foods and other methods of using these starches in foods are included herein.

In the examples which follow, all spray-drying nozzles are obtainable from Spraying Systems Co., Wheaton, Illinois. The following test procedures were used.

WATER SOLUBILITY MEASURE

A. Cold Water Solubility

The determination is carried out using distilled water at room temperature. About 0.5 g of starch is dispersed in 30–40 ml of water in a semi-micro stainless steel cup on a Waring blender base (Model 31B292). The blender is run at low speed while the starch is added (all at once) and then run at high speed for 2 minutes. The dispersion is immediately transferred to a 50 ml volumetric flask and diluted to 50 ml with water. A 25 ml portion of the stock dispersion (shaken well to ensure a homogenous dispersion) is removed by pipet and transferred to a 50 ml centrifuge tube. The sample is spun down at 1800–2000 rpms for 15 minutes. Once spun down, 12.5 ml of supernatant is pipetted into a 25 ml volumetric flask, 5 ml of 5N potassium hydroxide (KOH) are added with swirling, and the mixture is diluted with water. The remainder of the stock dispersion is shaken well, the insoluble starch dispersed with 10 ml of 5 N KOH while swirling. The mixture is diluted to 50 ml with water. The optical rotation of both the concentrated stock solution and the supernatant solution is measured.

$$\% \text{ Cold Water Solubles} = \frac{\text{Optical Rotation of Supernatant/Path Length of Supernatant}}{\text{Optical Rotation of Stock Solution/Path Length of Stock Solution}} \times 100$$

B. Hot Water Solubility

The procedure is the same as that described above except that boiling distilled water at 90°–100° C. (194°–212° F.) is used for dispersing the starch and all subsequent dilutions. No attempt is made to maintain temperature during the procedure.

WATER FLUIDITY MEASUREMENT

A. Water Fluidity (WF)

The water fluidity of the starches is measured using a Thomas Rotational Shear-Type Viscometer (manufactured by Arthur H. Thomas Co., Philadelphia, Pa. 19106), standardized at 30° C. with a standard oil having a viscosity of 24.73 cps, which oil requires 23.12±0.05 sec. for 100 revolutions. Accurate and reproducible measurements of the water fluidity are obtained by determining the time which elapses for 100 revolutions at different solids levels depending on the starch's degree of conversion (as conversion increases, the Water Fluidity increases and the viscosity decreases). The procedure used involves slurrying the required amount of starch (e.g., 6.16 g, dry basis) in 100 ml of distilled water in a covered copper cup and heating the slurry in a boiling water bath for 30 minutes with occasional stirring. The starch dispersion is then brought to the final weight (e.g., 107 g) with distilled water. The time required for 100 revolutions of the resultant dispersion at 81°–83° C. is recorded and converted to a water fluidity number of a conversion table.

TABLE I

| Time Required for 100 Revolutions (seconds) Amount of Starch Used (anhydrous, g): | | | | |
|---|---|---|---|---|
| 6.16[a] | 8.80[b] | 11.44[c] | 13.20[d] | Water Fluidity |
| 60.0 | | | | 5 |
| 39.6 | | | | 10 |
| 29.3 | | | | 15 |
| 22.6 | | | | 20 |
| 20.2 | | | | 25 |
| | 33.4 | | | 30 |
| | 27.4 | | | 35 |
| | 22.5 | | | 40 |
| | | 32.5 | | 45 |
| | | 26.8 | | 50 |
| | | 22.0 | | 55 |
| | | | 24.2 | 60 |
| | | | 19.2 | 65 |
| | | | 15.9 | 70 |
| | | | 13.5 | 75 |
| | | | 11.5 | 80 |
| | | | 10.0 | 85 |
| | | | 9.0 | 90 |

For a, b, c, and d, final weights of starch solutions are 107, 110, 113, and 115 g, respectively.

B. Calcium Chloride Viscosity (7.2% Solids Test)

The calcium chloride viscosity of the converted high amylose starch is measured using a Thomas Rotation Shear-Type Viscometer standardized at 30° C. (86° F.) with a standard oil having a viscosity of 24.73 cps, which oil requires 23.12±0.05 seconds for 100 revolutions. As the conversion of the starch increases, the viscosity of the starch decreases and the calcium chloride viscosity decreases. Accurate and reproducible measurements of the calcium chloride viscosity are obtained by determining the time which elapses for 100 revolutions at a specific solids level.

A total of 7.2 g of the converted starch (anhydrous basis) is slurried in 100 g of buffered 20% calcium chloride solution in a covered semi-micro stainless steel cup (250 ml capacity available from Eberbach), and the slurry is transferred to a glass beaker and is heated in a boiling water bath for 30 minutes with occasional stirring. The starch solution is then brought to the final weight (107.2 g) with hot (approximately 90°–100° C. (194°–212° F.)) distilled water. The time required for 100 revolutions of the resultant solution at 81°–83° C. (178°–181° F.) is measured three times in rapid succession and the average of the three measurements is recorded.

The calcium chloride solution is prepared by dissolving 264.8 g of reagent grade calcium chloride dehydrate in 650 ml of distilled water in a tared 1 L glass beaker. Thereafter 7.2 g of anhydrous sodium acetate is dissolved in the solution. The solution is allowed to cool and the pH is measured. If necessary, the solution is adjusted with hydrochloric acid to pH 5.6±0.1. The solution is then brought to weight (1007.2 g) with distilled water.

GEL PERMEATION CHROMATOGRAPHY

Starches were prepared for analysis by slurrying 5 mg of enzymatically debranched starch in 4 ml of dimethylaulfoxide ("DMSO") containing 0.3M sodium nitrate and heating the slurry to 80° C. for at least 30 minutes. Samples (200 ul) were injected into an ALC/GPC-150° C. Chromatograph (Waters Associates, Milford, Massachusetts) (equipped with a Nelson 3000 Series Chromatography Data System and two PLgel mixed 10 um columns (Polymer Laboratory, Amherst, Massachusetts), employing DMSO containing 0.03M sodium nitrate as the mobile phase), and diluted at a rate of 1 ml/min. The columns were calibrated using dextran standards (with molecular weights of 2,000; 20,000; 80,000; 500,000; and 2,000,000, obtained from Pharmacia Fine Chemicals, Piscataway, New Jersey). The percentage short chain amylose was calculated from the relative area of the peak obtained within the molecular weight range from about 500 to 20,000.

EXAMPLE 1

This example illustrates the preparation of soluble high amylose starch by the coupled jet-cooking/spray-drying process.

Part A

The process variables used for jet-cooking/spray-drying unmodified high amylose (about 70% amylose) corn starch are shown below, in Table II. A slurry of unmodified granular high amylose starch was fed into a jet-cooker (model C-15 available from National Starch and Chemical Company). Steam was metered into the slurry to cook the starch and the cooked starch was conveyed to a pneumatic atomization nozzle top mounted in a 35 foot tall, 16 foot diameter Hensey spray-dryer. Steam at 120 psig was used to atomize the starch. The atomized starch mist wall dried with air at 204° C. (40° F.).

TABLE II

| Process Conditions for Jet Cooking/Spray Drying High Amylose Starch | | |
|---|---|---|
| | Part A | Part B |
| Slurry Solids | 32.0% | 26.2% |
| Cook Solids | 28.0% | 25.0% |
| Jet Cooking Temperature °C. (°F.) | 143 (290) | 163 (325) |
| Steam Flow | 9.25 lb/min | — |
| Cook Flow | 3.8 gal/min | 6.5 gal/min |
| Nozzle Type[a] | 1J-152 | 1J-152 |
| Dryer Inlet Temp °C. (°F.) | 230–191 (446–375) | 230–191 (446–375) |
| Dryer Outlet Temp °C. (°F.) | 82–96 (180–205) | 82–96 (180–205) |
| Atomizing steam (psig) | 120.0 | 120 |

[a]Pneumatic nozzle obtained from Spraying System, Inc. (Model 1J; two-fluid).

The cold water solubility of the non-granular starch powder was 97.4% and the hot water solubility was greater than 99%.

Part B

Under process conditions shown above, in Table II,, a converted high amylose corn starch (about 70% amylose) was processed using the coupled jet-cooking/spray-drying process. A slurry of the starch was treated with 2.5% hydrochloric acid at 52° C. (126° F.) for 16 hours to give a converted starch having a calcium chloride viscosity of 25 seconds. After neutralization with sodium carbonate to a pH of about 6, the granular converted starch was filtered, washed and dried. The starch was then jet-cooked, and the jet-cooked starch dispersion was conveyed to a pneumatic atomization nozzle top mounted in a 35 foot tall, 16 foot diameter Hensey spray-dryer. The atomized starch mist was dried with air at 204° C. (400° F.).

The converted starch powder was 93.0% soluble in cold water and 97.1% soluble in hot water.

EXAMPLE 2

This example illustrates the preparation of soluble high amylose starch by steam-injection/dual-atomization or single-atomization spray-drying processes.

Unmodified granular corn starch containing about 70% amylose was slurried in water at 25.5% solids. This slurry was pumped by a Matt and Gaulin triplex pump at about 2.4 gallons per minute under about 5,000 psig to three steam atomization nozzles (dual-atomization nozzles as described in FIG. 1 of U.S. Pat. No. 4,280,851, issued Jul. 28, 1981, to Pitchon, et al.), mounted at the top of a 35 foot tall, 16 foot diameter Hensey spray-dryer. Steam at about 165 psig was used to gelatinize and atomize the starch. Air at 200° C. (396° F.) was used to dry the atomized starch mist.

The recovered granular pregelatinized starch powder had a cold water solubility of about 75 percent and a hot water solubility of about 95 percent.

EXAMPLE 3

This example illustrates the enzymatic preparation of starch containing soluble short chain amylose, and, optionally, long chain amylose, wherein the starch product comprises at least 40% total amylose.

PREPARATION OF THE DEBRANCHED STARCH

The starches were converted, crosslinked,, derivatized or dextrinized, where applicable, prior to gelatinization and treatment with a pullulanase enzyme. An aqueous slurry (20–30% solids) was prepared employing a native starch, or where applicable, a modified starch. The aqueous starch slurry was jet cooked at approximately 300° F. (149° C.) to gelatinize the starch. The cooked starch dispersion was placed in a constant temperature bath at 58°-60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucanohydrolase) which was used is a starch debranching enzyme produced by a novel species of Bacillus. This enzyme (Promozyme TM) was obtained from Novo Industri A/S of Denmark. The enzymatic activity of a 1.25 g/ml solution of Promozyme is standardized at 200 PUN/ml of solution. One PUN (Pullulanase Unit Novo) is the amount of enzyme which, under standard conditions, hydrolyzes pullulan, liberating reducing carbohydrate with a reducing power equivalent to 1 micro-mol glucose per minute. The procedure for determining PUN is available from Novo Industri A/S. Thus, for example, in a starch dispersion employing corn starch, 125 PUN of pullulanase per 100 g corn starch were added to the dispersion. For a waxy maize starch dispersion (with higher amylopectin content), 750 PUN of pullulanase per 100 g waxy maize starch were added to the dispersion.

The pullulanase was permitted to debranch the starch until at least a total of 40% amylose had been reached. The pullulanase was deactivated in preparing debranched starch by heating the dispersion to at least 80° C. The starch dispersion was spray-dried at an inlet temperature of 200°–210° C. and an outlet temperature of 120°–125° C. The spray dried-starch was screened through #40 mesh screen.

PREPARATION OF SHORT CHAIN AMYLOSE

Part A. Crystalline

A 28% solids slurry of waxy maize starch in water was jet cooked at 149° C. (300° F.) to yield a 25% solids starch dispersion. The dispersion was placed into a constant temperature water bath at 60° C., the pH was adjusted to 5.0, and 8 mls of the Promozyme pullulanase/100 g starch were added to the dispersion. The enzyme reaction was permitted to continue with continuous stirring for 88 hours.

Upon standing, a crystalline precipitate was formed in the milky starch dispersion. This precipitate was filtered, washed three times and air-dried to yield crystalline short chain amylose in about 85% yield. Gel permeation chromatography indicated the product contained 84% short chain amylose.

Part B. Soluble

A second dispersion of waxy maize starch was debranched in the same manner as Part A, except that the enzyme reaction was continued for 48 hours and filtering and washing steps were omitted. Thereafter the dispersion was spray-dried at 26% solids in a Niro laboratory spray-drier at an inlet temperature of 210° C. and an outlet temperature of 125° C. The product, which comprised 78% short chain amylose, was recovered in about 75% yield.

The starch was 100% soluble in cold and hot water.

EXAMPLE 4

This example illustrates the preparation of gelled canned meat products containing soluble high amylose starch which are used as pet foods.

Canned pet foods were prepared from the following formulations:

| | Canned Pet Food Formulation | | | | |
|---|---|---|---|---|---|
| | Percent By Weight | | | | |
| Ingredient | Control: No Starch | Control: Unmodified Corn Starch | Control: Converted Corn Starch[a] | High Amylose Starch[b] | High Amylose Starch[c] |
| Chicken Meat | 33.25 | 31.68 | 31.68 | 31.68 | 31.68 |
| Chicken Skin | 33.25 | 31.68 | 31.68 | 31.68 | 31.68 |
| Broth | 21.14 | 21.14 | 21.14 | 21.14 | 21.14 |
| Gizzard | 7.32 | 7.32 | 7.32 | 7.32 | 7.32 |
| Heart | 2.45 | 2.45 | 2.45 | 2.45 | 2.45 |
| Salt | 0.94 | 0.94 | 0.94 | 0.94 | 0.94 |
| Fried Onions | 0.63 | 0.63 | 0.63 | 0.63 | 0.63 |
| Starch | — | 3.14 | 3.14 | 3.14 | 3.14 |
| Sodium Nitrate Solution | 0.84 | 0.84 | 0.84 | 0.84 | 0.84 |
| Ground White Pepper | 0.10 | 0.10 | 0.10 | 0.10 | 0.10 |
| Ground Cloves | 0.04 | 0.04 | 0.04 | 0.04 | 0.04 |
| Ground Mace | 0.04 | 0.04 | 0.04 | 0.04 | 0.04 |

[a]Acid-converted to 60 WF.
[b]Prepared by the process of Example 2 from 70% amylose corn starch.
[c]Prepared by the process of Example 1 from 70% amylose corn starch which has been acid-converted to a 35 second calcium chloride WF.

The chicken meat, skin, heart and gizzards were parboiled in boiling water and then simmered for 30 minutes. The meats were ground in a Waring blender until a smooth paste was obtained. The seasonings were dry blended with the starch and added to 54° C. (130° F.) water in a blender. This mix was added to the meat paste and then the salt and fried onions were added. This material was mixed for 45 seconds, then heated to 60° C. (140° F.) and filled into cans. The cans were retorted at 15 pounds pressure, 116° C. (240° F.) for 1.5 hours, allowed to cool to room temperature and visually evaluated.

The evaluation showed that the control sample containing no starch did not form a gel, was soft and contained an undesirable amount of free oil. The unmodified corn starch sample was slightly better, but provided only a soft gel and slightly less oil than the control. The converted corn starch sample was slightly better than the unmodified corn starch sample, but also had undesirable gelling and oiling characteristics. Both of the soluble high amylose starch samples had cuttable, firm gels and no free oil.

EXAMPLE 5

This example illustrates the formulation of prefabricated, comminuted foods containing soluble, high amylose starch as a binder.

Part A. French Fried Potatoes

Prefabricated french fried potatoes were prepared from the following formulations:

| | Prefabricated French Fried Potatoes | |
|---|---|---|
| | Percent by Weight | |
| Ingredient | Control: No Starch | Soluble High Amylose Starch[a] |
| Dehydrated Potato[b] | 55.6% | 47.2% |
| Water | 43.98% | 43.98% |
| Starch | — | 8.4% |
| Onion Powder | 0.28% | 0.28% |
| Salt | 0.14% | 0.14% |

[a]Prepared by the process of Example 1 from 70% amylose corn starch which has been acid-converted to a 35 second calcium chloride WF.
[b]Potato granules obtained from the Pillsbury Company.

The salt, onion powder, starch and dehydrated potato were dry blended. Boiling water was added, and the mixture was mixed on low speed in a Mix Master mixer until a uniform mixture was obtained. This material was extruded into ½ inch strips and cut into 3½ inch pieces. These pieces were deep fat fried at 163° C. (325° F.) for 2.0 minutes, cooled and evaluated for crispness by five taste panelists.

Five out of five panelists indicated that the pieces made with the soluble high amylose starch exhibited a crispier product then the control. The structural integrity of the pieces were also noted as being superior to the control.

Part B. Surimi

Semi-thawed surimi (thawed for 1 hour at 25° C., 75% water) was chopped (using a Stephan VCM12 Cutter, 1500 rpm, cold-water jacketed) under vacuum with 2.5% salt for 9 minutes, followed by 3 minutes additional chopping with 5.0% starch (see Table III below) and ice-chilled water to adjust the water level to 78%. The quantities of salt and starch were added on a surimi weight basis. After chopping, the pate was loaded into a stuffer (Dick Vertical Hand Stuffer), packed into 30 mm diameter cellulose casings, and cooked at 90° C. for 40 minutes in a water bath. The gels were cooled immediately in running tap water for 20 minutes. After cooling, the casings were removed and the gels individually wrapped in cellophane to prevent interaction between the cellulose casing and the protein. The cooked surimi gels were equilibrated for 24 hours at room temperature prior to measuring gel strength.

The surimi gels were cut into cylindrical pieces (15 mm length, 30 mm diameter) and the gel strengths were measured by a Stevens LFRA Texture Analyzer (25 mm diameter probe, 0.5 mm/sec, 4 mm penetration). The average gel strength of 8 pieces was determined.

TABLE III

| Surimi Gel Strength | |
|---|---|
| Starch | grams/cm$^2$ |
| Soluble High Amylose$^a$ | 500 |
| Cornstarch | 430 |
| Waxy maize starch | 400 |
| High Amylose starch$^b$ | 300 |

$^a$Corn starch containing 70% amylose was solubilized by the process of Example 1.
$^b$Corn starch containing 70% amylose.

The sample containing soluble high amylose starch prepared by the coupled jet-cooking/srpay-drying process had the highest gel strength. Therefore, soluble high amylose starch provides desirable gel strength in surimi-type products, such as seafood and meat analogs, without requiring special cooking conditions typically employed to utilize conventional high amylose starches.

EXAMPLE 6

This example illustrates the formulation of instant gelling food products containing soluble high amylose starch.

Instant gelling desserts were prepared from the following formulation employing the starches listed in Table IV, below:

| Instant Lemon Pie Filling Formulation | |
|---|---|
| Ingredient | Percent By Weight |
| Baker Special Sugar | 76.86% |
| Lemon Crystals #7$^a$ | 3.23 |
| Sodium Citrate | 0.61 |
| Color$^{b,c}$ | 0.40 |
| Titanium Dioxide | 0.02 |
| Instant Starch$^d$ | 18.88 |

-continued

| Instant Lemon Pie Filling Formulation | |
|---|---|
| Ingredient | Percent By Weight |
| | 100.00% |

$^a$Obtained from Quest International Flavors & Fragrances, Glen Burnie, Maryland.
$^b$Yellow #5 at 1% on dextrose carrier.
$^c$McCormick yellow food coloring
$^d$See Table IV, below for description of starches.

A total of 156.5 grams of the dry ingredients were blended together and added to 335.5 grams of 49° C. (120° F.) (hot tap) water while mixing on the low speed setting of a Mix Master mixer for 2.0 minutes. Each sample was deposited in a graham cracker pie shell and refrigerated for 2 hours.

Samples were tested and visually evaluated by six taste panelists. Six out of six panelists indicated that the soluble high amylose starch prepared by the method of Example 1 formed a firmer gel than a modified pregelatinized starch used commercially in instant gelling dessert mixes.

Samples were tested for gel strength with a Stevens LFRA Texture Analyzer equipped with a 1.0 inch probe and set for a distance of 0.5 mm at a speed of 0.5 mm/second. Results are shown in Table IV.

TABLE IV

| Gel Strength of Lemon Pie Fillings | |
|---|---|
| Starch | grams/cm$^2$ |
| Crosslinked Converted Pregelatinized Tapioca starch$^a$ | 142 |
| Crosslinked Modified Pregelatinized Waxy Maize Starch$^b$ | No gel |
| Soluble High Amylose Starch$^c$ | 164 |
| Soluble High Amylose Converted Starch$^d$ | 180 |
| Soluble High Amylose Starch$^e$ | 164 |

$^a$Tapioca starch was crosslinked by treatment with POCl$_3$, acid-converted and drum-dried to pregelatinize the starch.
$^b$Waxy maize starch was crosslinked by treatment with POCl$_3$, derivatized by treatment with propylene oxide, drum-dried to pregelatinize the starch and then finely ground.
$^c$Corn starch containing 70% amylose was solubilized by the process of Example 1.
$^d$Corn starch containing 70% amylose was acid-converted to 35 second calcium chloride WF and solubilized by the process of Example 1.
$^e$Corn starch containing 70% amylose was solubilized by the process of Example 2.

Results indicate that soluble (or instant), high amylose starches provide superior gel strength in comparison with pregelatinized starches traditionally used in instant gelling desserts, such as instant lemon pie filling.

EXAMPLE 7

This example illustrates the preparation of liquid batters for foods formulated with soluble high amylose starch.

Battered chicken thigh pieces were prepared using the following batter: formulation:

| | Batter Formulation | | | | |
|---|---|---|---|---|---|
| | Controls | | Soluble High Amylose Starches | | |
| Ingredients | 1 | 2$^c$ | 2$^d$ | 3$^e$ | 4$^f$ |
| A. Dry Mix | Percent by Weight | | | | |
| Corn Flour$^a$ | 50 | 56 | 50 | 50 | 50 |
| Corn Flour$^b$ | 10 | — | — | — | 10 |
| Wheat Flour | 37 | — | 37 | 37 | 37 |
| Corn Flour | — | 37 | — | — | — |
| Starch | — | — | 10 | 10 | 4 |
| Sodium Aluminum Phosphate | 1.5 | 1.5 | 1.5 | 1.5 | 1.5 |
| Sodium Bicarbonate | 1.5 | 1.5 | 1.5 | 1.5 | 1.5 |
| B. Batter | | | | | |

-continued

| Batter Formulation | | | | | |
|---|---|---|---|---|---|
| | Controls | | Soluble High Amylose Starches | | |
| Ingredients | 1 | 2[c] | 2[d] | 3[e] | 4[f] |
| Dry mix (g) | 100 | 1.5 | 100 | 100 | 100 |
| Water (ml) | 240 | 1.5 | 240 | 240 | 240 |

[a]Micro-Crisp ® a high amylose corn flour obtained from National Starch and Chemical Company.
[b]Micro-Crisp ®D a modified high amylose corn flour obtained from National Starch and Chemical Company.
[c]Control containing no wheat flour. Corn flour (ordinary) was substituted for wheat flour.
[d]Waxy maize starch prepared by the method of Example 3 to contain 57% short chain amylose.
[e]Waxy maize starch prepared by the method of Example 3 to contain 30-35% short chain amylose.
[f]Corn starch containing 70% amylose prepared by the method of Example 1 and converted to a 35 second calcium chloride WF.

Batters were prepared by adding the dry mix to 100° F. water and mixing in a Waring blender at low speed for about 1 minute until uniform. Chicken thighs were parboiled for 15-20 minutes in boiling water, cooled to a handling temperature by rinsing in cold water and coated with about 2.5-3.0%, by weight, of a predust (N-Coat TM obtained from National Starch and Chemical Company). The predusted chicken was dipped in the batter, the percent batter pick-up was measured and recorded and the battered chicken was panfried at 185 to 188° C. (365°-370° F.) for about 1.5 minutes. The chicken was blast frozen for 15-20 minutes, then stored in a freezer until use.

The chicken was cooked to an internal temperature of about 150° F. (±100°F.) in a microwave oven (about 2.5 to 3.5 minutes) and evaluated for texture, appearance and crispness.

All batters formed an acceptable coating on the chicken. The wheat flour control had a pasty interface between the coating and the chicken. The non-wheat flour control had a lacy appearance more characteristic of bread crumbs than batter and a slightly bread-like interface between the chicken and the coating.

The debranched high amylose starches were preferred for crispness and appearance. They provided good film adhesion without a pasty interface. The color of these samples was preferred. The converted soluble high amylose starch prepared by the method of Example 1 provided a bready interface and a soggy surface and was not preferred for texture or appearance.

Thus, the debranched soluble high amylose starches herein provide improved batters for frozen prepared foods for use in microwave oven cooking.

EXAMPLE 8

This example illustrates the preparation of pasta and noodle products employing soluble high amylose starch.

Part A

Pasta (fettucini) was prepared according to the following formulation:

| | Fettucini Formulation | | | |
|---|---|---|---|---|
| | Percent By Weight | | | |
| | Starch Variable: | | | |
| Ingredient | No Starch | Soluble High Amylose Starch[a] | Soluble High Amylose Starch[b] | Converted Soluble High Amylose Starch[c] |
| Wheat Flour[d] | 58.23 | 52.40 | 52.40 | 52.40 |
| Salt | 0.28 | 0.28 | 0.28 | 0.28 |
| Egg | 34.66 | 34.66 | 34.66 | 34.66 |
| Cold Water | 6.83 | 6.83 | 6.83 | 6.83 |
| Starch | — | 5.83 | 5.83 | 5.83 |
| | 100.00 | 100.00 | 100.00 | 100.00 |

[a]Corn starch containing 70% amylose was processed as in Example 1.
[b]Corn starch containing 70% amylose was processed as in Example 2.
[c]Corn starch containing 70% amylose was acid-converted to 35 second calcium chloride WF and processed as in Example 1.
[d]All purpose flour (about 7% protein).

The flour was dry blended with the starch and salt. A well wall made in the center of the mixture and the eggs and water were added. The dough was mixed and allowed to sit (covered) for one hour at room temperature. The dough was rolled paper thin and again allowed to sit at room temperature for twenty minutes. The dough was cut into ¼ strips and sprinkled with corn meal. 100.0 g of pasta was boiled for 5.0 minutes, strained, rinsed with cold water and evaluated.

The pasta was evaluated for taste, texture and appearance by an eight-member panel. Seven out of the eight panelists chose the pasta containing soluble high amylose starch prepared according to Example 1 as the sample having the firmest texture after boiling. The control pasta had a slimy coating which the pasta containing high amylose starches did not. The pasta containing high amylose starch prepared according to Example 2 was also firmer than the control, but not as firm as the pasta containing starch prepared according to Example 1.

Part B.

Ramen noodles were prepared according to the following formulation:

| | Ramen Noodle Formulation | | | |
|---|---|---|---|---|
| | Percent By Weight | | | |
| | Control: No Starch | Soluble High Amylose Starch[b] | | Acetylated High Amylose Starch[c] | |
| Ingredients | | 1 | 2 | 3 | 4 |
| Wheat Flour[a] | 68.2 | 61.4 | 54.6 | 61.4 | 54.6 |
| Salt | 1.6 | 1.6 | 1.6 | 1.6 | 1.6 |
| Corn Oil | 1.0 | 1.0 | 1.0 | 1.0 | 1.0 |
| Water | 29.2 | 29.1 | 29.2 | 29.2 | 29.2 |
| Starch | — | 6.8 | 13.6 | 6.8 | 13.6 |

[a]Bread (patent) flour – 11% protein.
[b]Corn starch containing 70% amylose prepared by the method of Example 1.
[c]Acetylated corn starch containing about 50% amylose obtained from National Starch and Chemical Company.

The flour, salt, and corn oil were mixed in a food processor. While mixing, water was added very slowly to form a dough which was thoroughly mixed.

Using a pasta maker machine, the dough was rolled until it was even and smooth. The opening of the roller was gradually adjusted from 1 (widest) to 5 (desired width for noodles). The dough was cut with the pasta machine to produce noodles and dusted with flour (or starch, if starch is being used) after cutting to prevent sticking.

After cutting, the control noodles were very sticky and difficult to separate. The acetylated high amylose starch-containing noodles were not sticky, but at 20% became difficult to handle and the noodles were bundled too closely together. The soluble high amylose starch containing-noodles were the easiest to handle.

Noodles were loosely arranged on a plate placed on top of a small bowl in an enclosed pot of boiling water and steamed for 12 minutes (turned over after 6 minutes) until the noodles were a little shiny, slightly darker in color, and a little heavier/denser.

Noodles were air-dried with an industrial blow-dryer, then fried for 1 minute and 10 seconds in a pot of vegetable oil at 140° C. to remove moisture. The fried noodles were removed and placed on a paper towel. The noodles were air-dried again with an industrial blow-dryer and evaluated.

Samples were tested for fat content by an acid hydrolysis method (*Official Methods of Analysis of the Association of Official Analytical Chemists*, A.O.A.C., 14th Edition, 1984. Method #14.019). The sample containing 10% soluble high amylose starch contained only 3.22% fat, whereas the sample containing no starch had 6.0% fat after frying. The high amylose starch samples had a chewier texture than the flour control sample when evaluated in a taste test. Following prolonged exposure to hot water, the flour control sample was more sticky and mushy than the starch samples.

EXAMPLE 9

This example illustrates the preparation of french fried potatoes coated with soluble high amylose starch to improve potato texture.

Whole and unpeeled potatoes were held at 32° C. (90° F.) in water. Each potato was then peeled and cut into ¼ shoe strings, blanched in 82° C. (180° F.) water for 6 minutes, drained and dipped into the following coating solution for 28 seconds at 70° C. (150°-160° F.).

| | Potato Coating Solution | | | | | | |
|---|---|---|---|---|---|---|---|
| | | Controls | | Soluble High Amylose Starch | | | |
| Ingredient | No Starch | Acetylated High Amylose Starch[a] | High Amylose Starch[b] | 1[c] | 2[c] | 3[d] | 4[d] |
| Dextrose | 10.00 | 10.00 | 10.00 | 10.00 | 10.00 | 10.00 | 10.00 |
| SAPP[d] | 0.75 | 0.75 | 0.75 | 0.75 | 0.75 | 0.75 | 0.75 |
| Starch | — | 6.00 | 2.00 | 2.00 | 4.00 | 2.00 | 4.00 |
| Water | 89.25 | 83.25 | 87.25 | 87.25 | 85.25 | 87.25 | 85.25 |
| | 100.00 | 100.00 | 100.00 | 100.00 | 100.00 | 100.00 | 100.00 |

[a] Acetylated corn starch containing about 50% amylose obtained from National Starch and Chemical Company.
[b] Corn starch containing 70% amylose.
[c] Corn starch containing 70% amylose was solubilized as in Example 1.
[d] Corn starch containing 50% amylose was solubilized as in Example 1.
[d] Sodium acid pyrophosphate The shoe strings were hot air dried 93° C. (200° F.) to achieve a 20% moisture lose (weight loss), fried at 188° C. (370° F.) for 1.5 minutes, and allowed to drain on paper towels. Samples were reweighed to observe a weight change, and blast frozen (the samples were placed over dry ice with foil for 20 minutes until frozen). The potatoes were fried at 191° C. (375° F.) for 0.5-1.0 minutes.

The french fried potatoes were evaluated for crispness and appearance. The soluble high amylose starch samples containing 50% amylose were similar to those containing 70% amylose, except that the 70% amylose sample at 2% of the potato dip formulation was not as crisp as the other soluble high amylose formulations, and was similar to the no starch control. All experimental samples had a crisp exterior texture and a moist interior.

The acetylated high amylose starch sample (at 6% of dip) had more interior moisture than the soluble high amylose samples, was crisp, and was not as soggy as the no starch control and the high amylose starch (70%) control which had not been solubilized. The acetylated high amylose starch sample had a dry coating, whereas the soluble high amylose starch samples had a glazed appearance.

Thus, compared to a derivatized high amylose control, the soluble high amylose samples provided excellent surface texture and appearance when used in a french fried potato coating dip. These benefits were only marginal at low usage levels for 70% amylose starch (2% of dip) but clearly expressed at higher usage levels for 50% and 70% amylose starches (4% of dip).

EXAMPLE 10

This example illustrates the formulation of cookies employing soluble high amylose starch as a surface coating.

Cookies were prepared according to the following formulation:

| Cookie Formulation | |
|---|---|
| Ingredient | Percent By Weight |
| A. Starch[a] | 1.52 |
| Chocolate Morsels | 28.07 |
| Flour | 20.61 |
| Brown Sugar | 12.24 |
| Granulated Sugar | 10.13 |
| Baking Soda | 0.35 |
| Salt | 0.32 |
| B. Butter | 18.33 |
| Eggs | 8.88 |

[a] Pregelatinized crosslinked finely ground waxy maize starch obtained from National Starch and Chemical Company.

All of the ingredients in A were uniformly mixed and added to B. The cookie batter was mixed to a uniform dough and 23-24 grams were weighed per cookie. Cookies were predusted with the appropriate starch (see below), baked for 10.0 minutes at 191° C. (375° F.), cooled, and compared to control cookies with no predust.

| Cookie Surface Coatings |
|---|
| A. Corn starch containing 70% amylose solubilized by the process of Example 1. |

-continued

| Cookie Surface Coatings |
|---|
| B. Corn starch containing 70% amylose solubilized by the process of Example 1 and acid-converted to 35 second calcium chloride WF. |
| C. Corn starch containing 70% amylose solubilized by the process of Example 2. |
| D. Control - No Predust. |
| E. Control - Wheat Flour Product. |

Cookies were evaluated for taste, texture and appearance by a five-member taste panel. The panel agreed that the converted soluble high amylose starch prepared by the process of Example 1 gave the most crisp cookie, followed in preference by the soluble high amylose starch of Example 1, the soluble high amylose starch of Example 2, the wheat flour, and the no predust control.

EXAMPLE 11

This example illustrates the preparation of foods wherein soluble high amylose starch is employed as a gelatin extender or replacer.

Gelatin desserts were prepared according to the following formulation:

| | Gelatin Dessert Formulation | | | | |
|---|---|---|---|---|---|
| | Percent By Weight | | | | |
| | Starch: | | | | |
| Ingredient | A Control: No Starch | B Soluble High Amylose Starch[a] | C Soluble High Amylose Starch[b] | D control: Corn Starch | E Control: High Amylose Starch[c] |
| Gelatin | 25 | 17.6 | 17.5 | 17.5 | 17.5 |
| Baker Special Sugar | 75 | 75.0 | 75.0 | 75.0 | 75.0 |
| Starch | — | 7.5 | 7.5 | 7.5 | 7.5 |
| | 100 | 100.0 | 100.0 | 100.0 | 100.0 |

[a]Corn starch containing 70% amylose solubilized by the process of Example 1.
[b]Corn starch containing 70% amylose solubilized by the process of Example 1 and acid-converted to 35 second calcium chloride WF.
[c]Corn starch containing 70% amylose.

The gelatin, sugar and starch were dry blended. A total of 120.0 g of boiling water was added to a blender cup and the dry ingredients were slowly added while mixing on slow speed for 30 seconds, and 120.0 grams of cold water was added and mixing continued for an additional 30 seconds. The solution was poured into 4 oz. glass jars and refrigerated for 12 hours. Gel strengths were taken on a Stevens LFRA texture analyzer set at 0.5 mm distance and 0.5 mm/sec, with a 1.0 inch probe. Results are listed in Table V, below.

TABLE V

| Gelatin Dessert Formulation | Gel Strength (grams) |
|---|---|
| A Control - Gelatin | 170[b] |
| B Example 1 Starch | 148[b] |
| C Example 1 Starch | 99[b] |
| D Control - Corn Starch | 30[a] |
| E Control - High Amylose Starch | 28[a] |

[a]Weak gel, thin, no body.
[b]Acceptable gels.

Results show that replacement of 30% of the gelatin in a gelatin dessert formulation with soluble high amylose starch results in an excellent gel. Some clarity was lost at the 30% replacement level, but desserts were otherwise acceptable. The corn starch and high amylose starch controls did not gel at the temperatures used to prepare gelatin desserts.

EXAMPLE 12

This example illustrates the formulation of an external coating to prevent browning in sliced or cut fresh fruits and vegetables employing soluble high amylose starch.

An external coating solution was prepared according to the following formulation:

| Fruit/Vegetable Coating Formulation | | |
|---|---|---|
| | Percent By Weight | |
| Ingredient | Control | Test |
| Water | 100 | 85 |
| Starch | — | 15 |

The water was boiled and placed in a Waring blender at 88° C. (190° F.). The starch was added and mixed for 30 seconds. The slurry was applied to sliced and peeled apples at 60° C. (140° F.) allowed to air dry. The time required for browning to appear and the degree of browning were recorded. Results are shown in Table VI

TABLE VI

| | Apple Slice Browning | |
|---|---|---|
| Sample | Time to Initial Browning | Degree of Browning[d] (1 = white; 10 = brown) |
| A No Starch | 2 min. | 10 |
| B Soluble High Amylose Starch[a] | 28 hours[e] | 1–2 |
| C Soluble High Amylose Starch[b] | 3 hours[f] | 7 |
| D Soluble High Amylose Starch[c] | 28 hours | 2 |
| E Unmodified Corn Starch | 4 min. | 9 |

[a]Corn starch containing 70% amylose acid-converted to 35 second calcium chloride WF and solubilized by the process of Example 1.
[b]Corn starch containing 70% amylose solubilized by the process of Example 1.
[c]Waxy maize starch containing 45-55% short chain amylose solubilized by the process of Example 3.
[d]Observations were made 5 hours after apples were dipped into starch dispersions.
[e]No browning was observed during test. Samples dried out.
[f]Starch dispersion left a thick, plastic, heavy coating on apples.

Results show that the soluble high amylose starch dispersions were effective in preventing browning on the cut surface of fresh fruit. The converted starch and short chain amylose-containing (debranched) starch provided optimum protection against browning. The samples containing no starch or unmodified corn starch were ineffective in preventing browning.

EXAMPLE 13

This example illustrates the use of soluble high amylose starch in manufacturing breading crumbs for coating foods prior to cooking.

Part A

Bread and bread crumbs were prepared by the following formulation and processes:

| Bread Dough Formulation Quantity in Grams | | | | | | | | | |
|---|---|---|---|---|---|---|---|---|---|
| | Controls: No Starch | | Soluble High Amylose Starch | | | | | | |
| Ingredient: | 1 | 2 | 3[a] | 4[b] | 5[c] | 6[d] | 7[e] | 8[f] | 9[g] |
| Flour | 1,000 | 1,000 | 800 | 800 | 812 | 800 | 800 | 800 | 800 |
| Starch | — | — | 200 | 200 | 188 | 200 | 200 | 200 | 200 |
| Water | 635 | 570 | 835 | 873 | 570 | 770 | 770 | 876 | 425 |
| Salt | 20 | 20 | 20 | 20 | 20 | 20 | 20 | 20 | 20 |
| Non-fat Dry Milk | 20 | 30 | 20 | 30 | 30 | 30 | 30 | 30 | 30 |
| Shortening | 30 | 30 | 30 | 30 | 30 | 30 | 30 | 30 | 30 |
| High Fructose Corn Syrup | 80 | — | 80 | — | — | — | — | — | — |
| Sugar | — | 60 | — | 60 | 60 | 60 | 60 | 60 | 60 |
| Yeast | 20 | 20 | 20 | 20 | 20 | 20 | 20 | 20 | 20 |
| | 1,805 | 1,730 | 2,033 | 2,033 | 1,730 | 1,930 | 1,930 | 2,036 | 1,585 |

[a] Corn starch containing 70% amylose solubilized by the method of Example 1.
[b] Corn starch containing 70% amylose acid-converted to 35 second calcium chloride WF and solubilized by the process of Example 1.
[c] Same starch as "a", above, except containing 50% amylose.
[d] Corn starch containing 70% amylose solubilized by the method of Example 2.
[e] Corn starch containing 50% amylose solubilized by the method of Example 2.
[f] Corn starch containing 70% amylose debranched and solubilized by the method of Example 3.
[g] Waxy maize starch debranched and solubilized by the method of Example 3.

The dough was prepared by one of three processes described below (see Table VII) and then the bread was baked and bread crumbs were prepared as described below.

1. Cold Process Dough

One-half of the water 43° C. (110° F.) was mixed with the yeast. A dry blend of one-half of the flour, one-half of the starch (except in the no starch control), and the non-fat dry milk was placed in the bowl of a Hobart mixer and mixed well for about 30 seconds with the remaining water and the corn syrup. The yeast suspension and remaining flour and starch were blended into the mixture for 2 to 3 minutes. The shortening and salt were added and the dough was mixed until smooth and elastic. The dough was proofed in a humidity cabinet (27° C. (80° F.) and 90% humidity) for 4 hours.

The dough was degassed, weighed into 700 g aliquots, placed in greased pans and proofed for an additional hour. The loaves were baked at 232° C. (450° F.) for 14 to 18 minutes, cooled and weighed and measured. The bread was sliced, air-dried overnight and ground in a Fitz Mill using a ¼ inch screen. The resulting crumbs were toasted to 5% moisture.

2. Hot Process Dough

Bread crumbs were prepared by the same method as described above for Cold Process Dough except that: (1) the yeast was mixed with 235 g of water; (2) the remaining water was heated to 88° C. (190° F.) and mixed with the starch in the Hobart mixer with a stir paddle for about 5 minutes and cooled to 60° C. (140° F.); and (3) the starch dispersion was mixed with the non-fat dry milk, corn syrup and one-half of the flour with agitation for 30 seconds.

3. Blender Hot Process Dough

The dough was prepared as described above for Hot Process Dough except that the yeast was mixed with only 135 g of water and the remaining water was added to a warmed Waring Blender at 88° C. (190° F.). The starch was slowly added to the water with blending until the starch was dispersed. The starch dispersion was placed on a steam table for 15 minutes, weighed, water was added to bring dispersion back to original weight, as needed, and the dispersion was cooled with stirring to about 60° C. (140° F.). The procedure was continued as described above in Processes 1 and 2.

Results of bread loaf and bread crumb evaluations are set forth in Table VII.

TABLE VII

| | | Evaluation of Bread and Bread Crumb | | |
|---|---|---|---|---|
| | | Bread (After Baking) | | |
| Sample[a,c] | Dough Quality | Weight (g) | Height (cm) | Description |
| Controls | | | | |
| 1 | Wet, Spidery, sponge-like, rose well | 670 | 7.9 | Good Browning and crumb structure |
| 2 | Smooth, not sticky | 486 | 8.5 | Good crumb, open structure, browned |
| Soluble High Amylose Starches | | | | |
| 3[b] (1) Cold Process | Dry, cracks when stretched | 667 | 5.8 | Did not rise well, poor browning, dense crumb |
| (2) Hot Process | Wet, gummy, lumpy | 662 | 6.1 | Did not rise well, poor browning, dense crumb |
| (3) Blender Hot Process | Wet, gummy, rose well | 645 | 5.3 | Did not rise well, poor surface browning, dense moist crumb |
| 4 | Some lumps | 492 | 5.9 | Short texture, dense crumb, light color |
| 5 | Smooth, not sticky | 497 | 6.5 | Dense crumb, browned |
| 6 | Sticky, does not form a ball | 481 | 7.3 | Rose well, browned, dense crumb |
| 7 | Sticky, does not form a ball | 489 | 8.1 | Rose well, browned, dense crumb |
| 8 | Dry, tears, lumpy | 484 | 5.3 | Some lumps, dense moist crumbs |
| 9 | Sticky, does not form a ball, tears | 324 | 6.9 | Browned, dense moist crumbs, center slightly doughy |

[a] Samples are described above in Bread Formulation Table.
[b] Sample 3 was prepared by each of the three processes described above.
[c] Except for Sample 3, breads containing soluble high amylose starch were prepared by the Blender Hot Process described above, as was control 2. Control 1 was prepared by the Cold Process.

All soluble high amylose starches produced an acceptable bread loaf. The replacement of about 20% of the flour (wheat) with starch caused a loss of total gluten and less bread rise and a more dense crumb in experimental samples. Preferred breads included those soluble high amylose starches which were neither converted nor debranched.

Thus, bread and bread crumbs may be formulated to contain soluble high amylose starches.

Part B

The crumbs prepared in Part A, above, from Control Sample 1 (prepared by the Cold Process) and soluble high amylose starch Sample 3 (prepared by Cold Process, Hot Process and blender Hot Process) were evaluated in battered and breaded fish pieces for adhesion, crispness, oiliness and color. Results are shown in Table VIII, below.

The breaded fish was prepared by battering frozen fish pieces with the wheat flour control (1) batter described in Example 7, coating the fish with bread crumbs and deep-fat-frying the fish for 5 minutes in oil at 193°–204° C. (380°–400° F.). Prior to battering the fish it was dipped in warm water and dusted with wheat flour.

TABLE VIII

Evaluation of Breaded Fried Fish

| Sample[a] | Adhesion | Crispness | Oiliness | Color |
|---|---|---|---|---|
| Control | | | | |
| 1 | Very good | Good | Very oily | Golden brown |
| Soluble High Amylose Starch | | | | |
| 3-1 | Good | Good | Moderately oily | Golden brown and lighter spots |
| 3-2 | Good | Good | Moderately oily | Dark, golden brown |
| 3-3 | Good | Very good | Moderately oily | Golden, lighter spots |

[a] See Bread Dough Formulation, above for a description of the starches used in these samples.

The results show that soluble high amylose starch is an effective barrier to oil pick-up and migration in breaded, fried foods. This benefit was observed in all samples and was independent of whether the starch was initially dispersed in hot or cold water. The starch sample which was dispersed in hot water with agitation in a blender before bread formulation was preferred for crispness and color in the final breaded, fried fish product.

Now that the preferred embodiments of the present invention have been described in detail, various modifications and improvements thereon will become readily apparent to those skilled in the art. Accordingly, the spirit and scope of the invention are to be limited only by the appended claims, and not by the foregoing specification.

We claim:

1. An improved method for manufacturing food(s), selected from the group consisting of imitation cheese, gelled canned pet food, prefabricated French-fried potatoes, cut fresh fruits and vegetables, coated French-fried potatoes, pasta, gelatin desserts, surimi, batter-fried foods, breaded foods, microwavable batter-fried foods, microwavable breaded foods, cookies, instant gelling desserts, cheese analogs, gelled meat substitutes, Ramen noodles, and bread crumbs, comprising the steps of:
a) dispersing in an aqueous medium at a temperature of 0 to 100° C. a powdered component comprising from 10 to 90%, by weight, of a soluble high amylose starch selected from the group consisting of (i) spray-dried, non-granular high amylose starch, characterized in that the starch is substantially non-crystalline, substantially non-retrograded, and fully predispersed; (ii) spray-dried, uniformly gelatinized high amylose starch in the form of granular indented spheres, with at least a majority of the granules being whole and unbroken, these starch granules being in the form of loosely-bound agglomerates of individual granules; and (iii) enzymatically debranched, gelatinized starch, comprising at least 40% amylose; and (iv) mixtures thereof; and
b) manufacturing the food(s) with the dispersed powdered component; wherein the food(s) are manufactured with soluble high amylose starch under atmospheric pressure and temperature conditions.

2. The method of claim 1, wherein the soluble high amylose starch (i) is prepared by a process comprising the steps of:
(a) forming a slurry or a paste comprising a converted or unconverted high amylose starch and water;
(b) jet-cooking the slurry or paste of the starch with steam at a temperature sufficient to fully disperse or solubilize the starch;
(c) immediately conveying and introducing the jet-cooked starch into a nozzle of a spray-dryer at substantially the same temperature and pressure as the jet-cooking step;
(d) atomizing the jet-cooked dispersion or solution through the nozzle of the spray-dryer;
(e) drying the atomized mist of the jet-cooked starch within the spray-dryer; and
(f) recovering the jet-cooked and spray-dried starch as a water-soluble powder.

3. The method of claim 1, wherein the soluble high amylose starch (ii) is prepared by a process comprising the steps of:
(a) slurrying the starch in an aqueous medium;
(b) atomizing the starch into an enclosed chamber;
(c) interjecting a heating medium into the atomized slurry in the enclosed chamber to cook the starch, said chamber containing a vent aperture positioned to enable the atomized slurry to exit the chamber, the size and shape of the chamber and the vent aperture being effective to maintain the temperature and moisture content of the material for a period of time sufficient to cook the starch; and
(d) drying the atomized starch.

4. The method of claim 1, wherein the soluble high amylose starch (ii) is prepared by a process comprising the steps of:
(a) slurrying the starch in an aqueous medium;
(b) feeding a stream of the starch at a pressure from about 50 to 250 psig into an atomizing chamber within a spray-drying nozzle;
(c) injecting a heating medium into the atomizing chamber at a pressure from about 50 to 250 psig;
(d) simultaneously cooking and atomizing the starch slurry as the heating medium forces the starch through a vent in the chamber; and
(e) drying the atomized starch.

5. The method of claim 1, wherein the soluble high amylose starch (iii) is prepared by a process comprising the steps of:
(a) providing a pregelatinized starch;
(b) hydrolyzing alpha-1,6-D-glucosidic bonds of the starch with an alpha-1,6-D-glucanohydrolase until the starch comprises at least 40%, by weight, amylose; and
(c) recovering the starch in a soluble powder.

* * * * *